(12) United States Patent
Otto

(10) Patent No.: US 12,076,024 B2
(45) Date of Patent: Sep. 3, 2024

(54) ROTATABLE BLADE GUARD FOR SURGICAL SAW

(71) Applicant: MAKO Surgical Corp., Weston, FL (US)

(72) Inventor: Jason Karl Otto, Sioux Falls, SD (US)

(73) Assignee: MAKO Surgical Corp., Weston, FL (US)

( * ) Notice: Subject to any disclaimer, the term of this patent is extended or adjusted under 35 U.S.C. 154(b) by 140 days.

(21) Appl. No.: 17/852,412

(22) Filed: Jun. 29, 2022

(65) Prior Publication Data

US 2023/0008215 A1    Jan. 12, 2023

Related U.S. Application Data

(60) Provisional application No. 63/219,655, filed on Jul. 8, 2021.

(51) Int. Cl.
*A61B 17/14* (2006.01)
*A61B 17/00* (2006.01)
*A61B 90/00* (2016.01)

(52) U.S. Cl.
CPC .......... *A61B 17/142* (2016.11); *A61B 17/147* (2016.11); *A61B 2017/00017* (2013.01); *A61B 2090/0801* (2016.02)

(58) Field of Classification Search
CPC ................ A61B 17/142; A61B 17/147; A61B 2017/00017; A61B 2090/0801; A61B 2090/062
See application file for complete search history.

(56) References Cited

U.S. PATENT DOCUMENTS

| | | | |
|---|---|---|---|
| 1,942,766 A * | 1/1934 | O'Banion | A61F 15/02 30/276 |
| 2,367,432 A * | 1/1945 | Reprogle | A61F 15/02 606/176 |
| 3,781,988 A | 1/1974 | Jones | |
| 5,071,426 A | 12/1991 | Dolgin et al. | |
| 6,001,115 A | 12/1999 | Ahola et al. | |
| 6,560,873 B1 | 5/2003 | Ortner et al. | |
| 6,893,334 B1 | 5/2005 | Stivers | |
| 7,725,162 B2 | 5/2010 | Malackowski et al. | |
| 7,857,824 B2 | 12/2010 | Kiehne | |
| 8,010,180 B2 | 8/2011 | Quaid et al. | |
| 8,894,654 B2 | 11/2014 | Anderson | |
| 9,119,655 B2 | 9/2015 | Bowling et al. | |
| 9,247,954 B2 | 2/2016 | Nallakrishnan | |

(Continued)

FOREIGN PATENT DOCUMENTS

WO    2021011646 A2    1/2021

*Primary Examiner* — Julian W Woo
(74) *Attorney, Agent, or Firm* — Howard & Howard Attorneys PLLC

(57) ABSTRACT

A surgical saw assembly that is adapted for cutting an anatomy. The surgical saw assembly includes a blade guard that supports a saw blade prevent deflection or skiving of the saw blade. The blade guard is rotatably moveable and has a front edge profile that interacts with a surface of the anatomy. The front edge profile has a geometry that is at least partially curved and/or follows a non-linear path of movement to provide a smooth interaction between the blade guard and the surface of the anatomy during rotational cuts that are not directly normal to the anatomical surface.

20 Claims, 11 Drawing Sheets

(56) References Cited

U.S. PATENT DOCUMENTS

| | | | |
|---|---|---|---|
| 9,566,122 B2 | 2/2017 | Bowling et al. | |
| 10,940,599 B2 | 3/2021 | Reyes et al. | |
| 11,166,775 B2 | 11/2021 | Gilhooley et al. | |
| 11,219,465 B2 | 1/2022 | Guzman et al. | |
| 11,376,016 B2 * | 7/2022 | Nunan | A61B 17/142 |
| 2012/0330429 A1 | 12/2012 | Axelson, Jr. et al. | |
| 2014/0180290 A1 | 6/2014 | Otto et al. | |
| 2017/0348007 A1 | 12/2017 | Shiels | |
| 2018/0186018 A1 | 7/2018 | Peyrot | |
| 2019/0083191 A1 | 3/2019 | Gilhooley et al. | |

\* cited by examiner

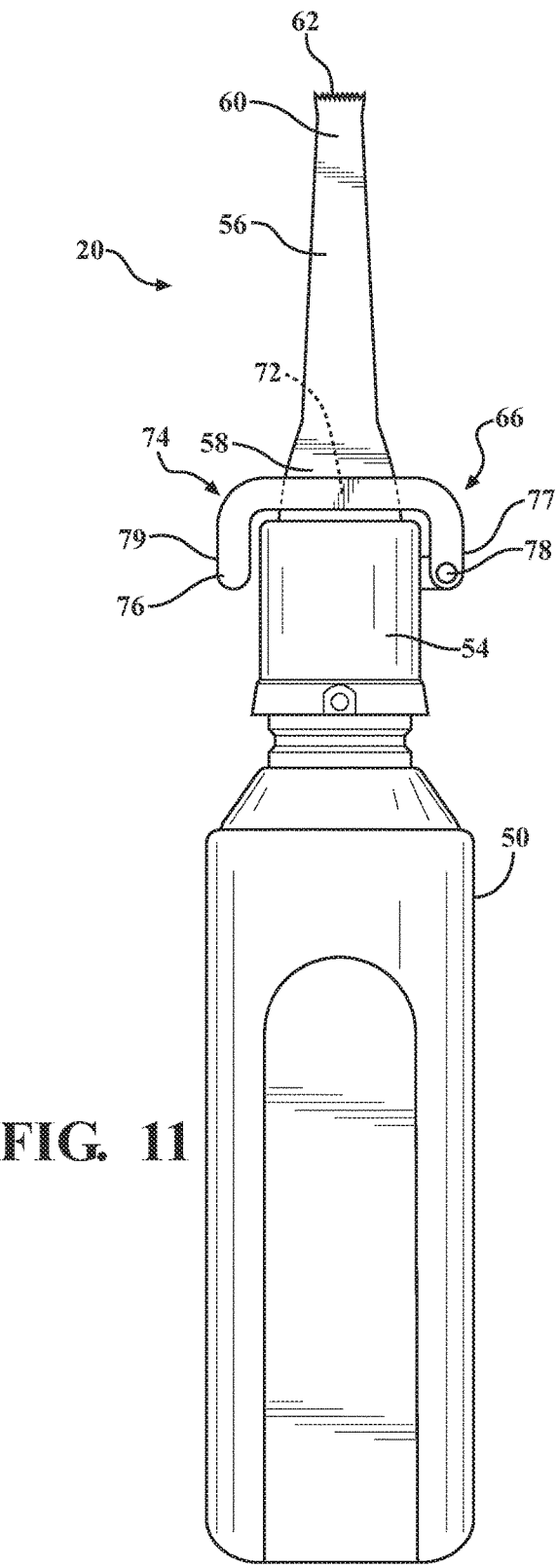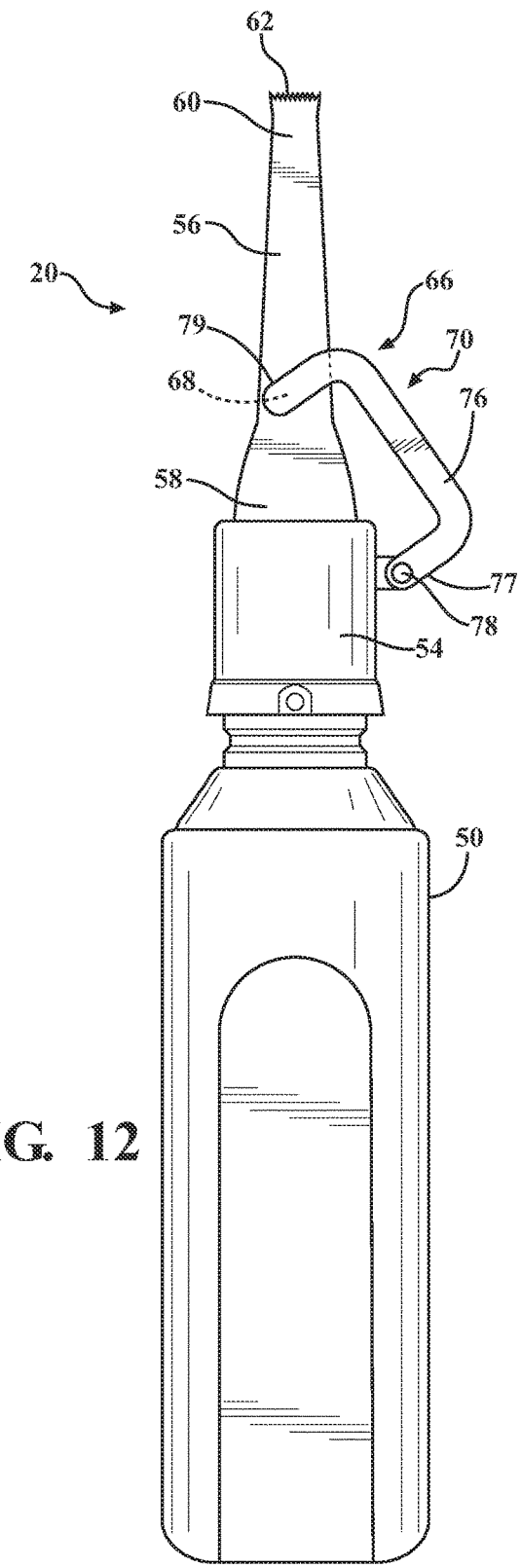

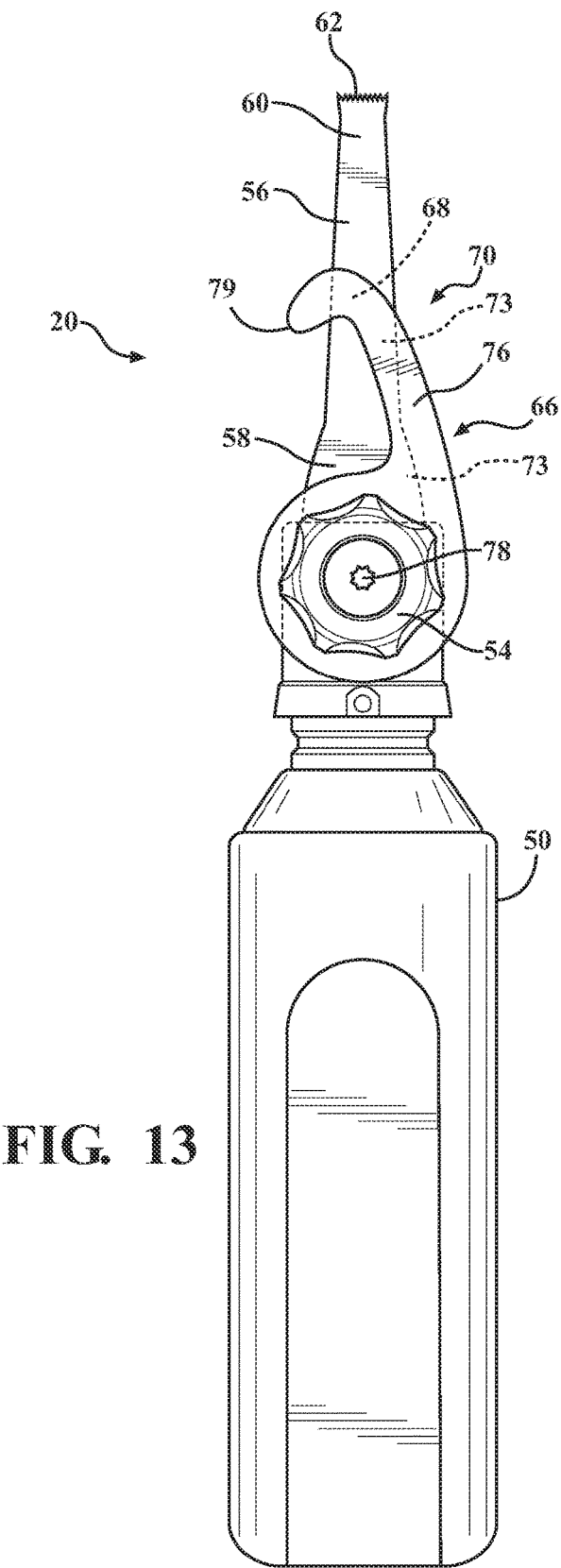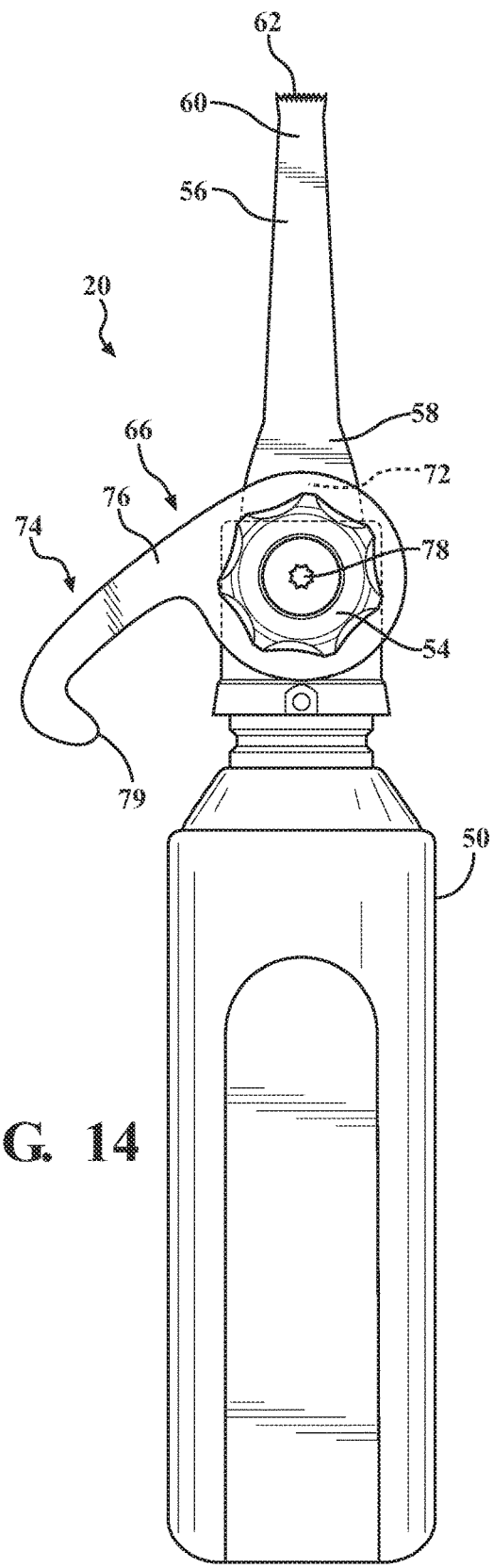

ROTATABLE BLADE GUARD FOR SURGICAL SAW

CROSS-REFERENCE TO RELATED APPLICATIONS

The subject application claims priority to and all the benefits of U.S. Provisional Patent App. No. 63/219,655, filed on Jul. 8, 2021, the entire contents of which is hereby incorporated by reference.

TECHNICAL FIELD

The disclosure generally relates to techniques for supporting a saw blade with a blade guard of a surgical device.

BACKGROUND

It is prevalent to use powered surgical saw assemblies during surgical procedures. Generally, these surgical saw assemblies may be operated by a user such as a surgeon or may be operated by a robotic cutting system. The surgical saws include a saw blade which is configured to cut hard tissue of a patient, such as bone. For example, saw blades are used in total knee arthroplasty, total hip arthroplasty, and similar types of procedures to create planar cuts on the bone.

In conventional surgical saws, the saw blade can undergo undesirable deflection or skiving (e.g., deviation from an intended cut plane and/or deviation from an intended entry point) during the cutting process, and most prevalently, during the initial cut of the hard tissue with the saw blade. Such deflection or skiving can be particularly difficult to control when making an initial cut on non-flat portions of hard tissue, such as at the ends of a femur (e.g., condyles, femur head).

One option to reduce skiving or deflection is to employ a blade support to hold a portion of the saw blade in place during surgical cuts. There have been attempts to provide blade supports that uses a retractable member moveable only in a linear direction along the length of the saw blade. Such conventional linear blade supports are less effective and less robust when making rotational (e.g., yaw) surgical cuts that are not directly normal to the bone surface because the movement of retractable member is limited to one linear direction. Also, conventional retractable members typically have a straight edge, which is not ideal for interacting with complex bone surfaces. In other words, interaction between the straight edge and the complex bone surface can cause the blade support to flex or bend causing interference with the saw blade. Furthermore, conventional linear blade supports typically have a bulkier configuration by requiring rods which hold the blade support. These rods, whether fixed or retractable, are elongated and can interfere with the surgical site. Furthermore, even when fully retracted, conventional linear blade supports typically have components that extend into the saw blade area, thereby potentially reducing the maneuverability of the surgical saw relative to the anatomy.

There is an opportunity to overcome one or more of the aforementioned challenges.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a surgical saw assembly is provided which is adapted for cutting an anatomy, the surgical saw assembly comprising: a base including a motor and a drive hub; a saw blade including an attachment portion configured to be removably coupled to the drive hub and including a cutting portion comprising a plurality of teeth; and a blade guard being coupled to one or more of the base or the saw blade and being rotatably moveable relative to the saw blade to support the saw blade, and wherein the blade guard comprises a front edge profile that is configured to interact with a surface of the anatomy and wherein the front edge profile is configured to follow a non-linear path of movement.

According to a second aspect, a surgical device is provided for use with a saw blade and being adapted for cutting an anatomy, the surgical device comprising: a base including a motor and a drive hub for removably receiving the saw blade; and a blade guard being adapted to support the saw blade, the blade guard being coupled to the base and being rotatably moveable, and wherein the blade guard comprises a front edge profile that is configured to interact with a surface of the anatomy and wherein the front edge profile is configured to follow a non-linear path of movement.

According to a third aspect, a surgical saw assembly is provided which is adapted for cutting an anatomy, the surgical saw assembly comprising: a base including a motor and a drive hub; a saw blade including an attachment portion configured to be removably coupled to the drive hub and including a cutting portion comprising a plurality of teeth; and a blade guard being coupled to one or more of the base or the saw blade and being rotatably moveable relative to the saw blade to support the saw blade, and wherein the blade guard comprises a front edge profile that is configured to interact with a surface of the anatomy and wherein the front edge profile has a geometry that is at least partially curved.

According to a fourth aspect, a surgical saw assembly is provided comprising: a base including a motor and a drive hub; a saw blade including an attachment portion configured to be removably coupled to the drive hub and including a cutting portion comprising a plurality of teeth, and the saw blade having a length defined between the attachment portion and the cutting portion; and a blade guard configured to support the saw blade, the blade guard being coupled to one or more of the base or the saw blade and rotatably moveable between a first position and a second position, wherein in the first position the blade guard is configured to support the saw blade at a first location along the length of the saw blade and in the second position the blade guard is configured to support the saw blade at a second location along the length of the saw blade, the first location being further from the attachment portion than the second location.

According to a fifth aspect, a surgical device is provided for use with a saw blade including an attachment portion and a cutting portion comprising a plurality of teeth, and the saw blade having a length defined between the attachment portion and the cutting portion, the surgical device comprising: a base including a motor and a drive hub for removably receiving the saw blade; and a blade guard for supporting the saw blade, the blade guard being coupled to the base and rotatably moveable between a first position for supporting the saw blade at a first location along the length of the saw blade, and a second position for supporting the saw blade at a second location along the length of the saw blade, the first location being further from the attachment portion than the second location.

According to a sixth aspect, a surgical device is provided for use with a saw blade, the surgical device comprising: a base including a drive hub for receiving the saw blade; and a blade guard for supporting the saw blade and being coupled to the base and rotatably moveable between a first position and a second position, wherein in the first position the blade guard is further from the base than in the second position.

According to a seventh aspect, a surgical device is provided comprising: a base including a drive hub; and a blade guard being coupled to the base, wherein the blade guard is rotatably moveable.

According to an eighth aspect, a saw blade is provided comprising: a blade body including an attachment portion, a cutting portion opposite the attachment portion including a plurality of teeth, and the blade body comprising a length defined between the attachment portion and the cutting portion; and a blade guard coupled to the blade body and being rotatably moveable between a first position and a second position, wherein in the first position the blade guard is configured to support the blade body at a first location along the length and in the second position the blade guard is configured to support the blade body at a second location, the first location being further from the attachment portion than the second location.

According to a ninth aspect, a method of operating a surgical saw assembly or device of any preceding aspect is provided.

According to a tenth aspect, a method of operating a surgical saw assembly is provided, the surgical saw assembly comprising a base including a motor and a drive hub, a saw blade including an attachment portion coupled to the drive hub and a cutting portion comprising a plurality of teeth, and the saw blade having a length defined between the attachment portion and the cutting portion, and a blade guard being coupled to one or more of the base or the saw blade and rotatably moveable between a first position and a second position, the method comprising: placing the blade guard is in the first position for supporting the saw blade at a first location along the length of the saw blade; and rotatably moving the blade guard from the first position to the second position for supporting the saw blade at a second location along the length of the saw blade.

Any of the above aspects can be combined in part, or in whole.

BRIEF DESCRIPTION OF THE DRAWINGS

Advantages of the present disclosure will be readily appreciated as the same becomes better understood by reference to the following detailed description when considered in connection with the accompanying drawings wherein:

FIG. 11 is a top view of another example of a surgical saw assembly having a blade guard in a first position.

FIG. 12 is a top view of the surgical saw assembly of FIG. 11 having the blade guard in the second position.

FIG. 13 is a top view of yet another example of a surgical saw assembly having a blade guard in a first position.

FIG. 14 is a top view of the surgical saw assembly of FIG. 13 having the blade guard in the second position.

DETAILED DESCRIPTION

I. Example System Overview

Figure 1:
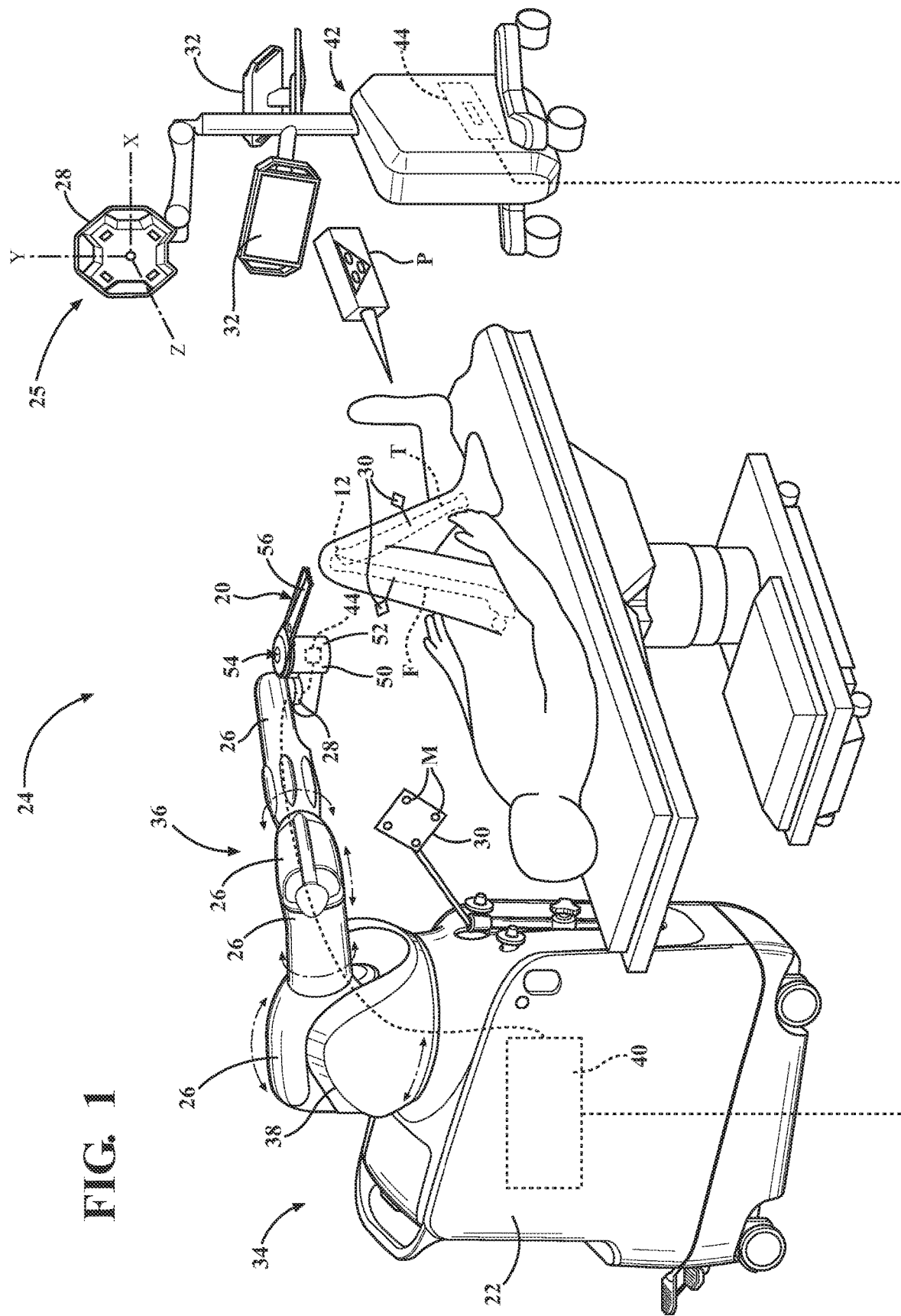
FIG. 1 is a perspective view of an robotic cutting system in an operating room, according to one example.
Figure 2:
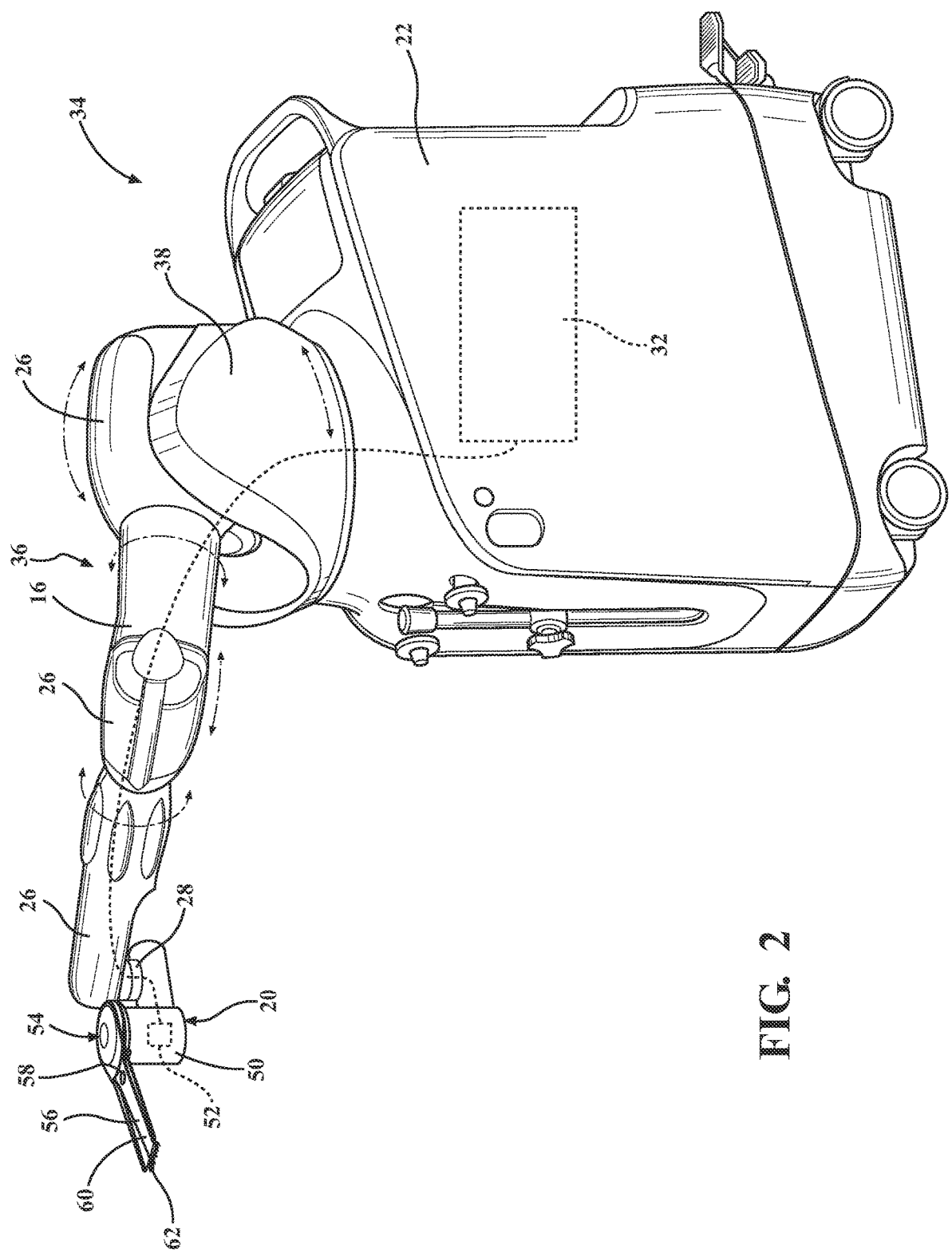
FIG. 2 is a perspective view of a robotic manipulator including a surgical saw assembly, according to one example.

Referring to the Figures, a surgical saw assembly 20 is shown for use during surgical procedures. The surgical procedures may be orthopedic surgeries, brain surgeries, or any other surgeries requiring the use of a cutting instrument. The surgical procedure includes the cutting of hard tissue, such as bone or the like. In some examples, the surgical procedure involves partial or total knee, hip, or shoulder replacement surgery, or may involve spine surgery.

The surgical saw assembly 20 is designed to cut away material. In some cases, the material (e.g., bone) is to be replaced by surgical implants such as hip, knee, shoulder, and spine implants, including unicompartmental, bicompartmental, or total knee implants, acetabular cups, femur stems, humerus implants, and the like. Some of these types of implants are disclosed in U.S. Patent Application Publication No. 2012/0330429, entitled, "Prosthetic Implant and Method of Implantation," the entire disclosure of which is hereby expressly incorporated by reference herein. It should be appreciated that the systems and methods disclosed herein may be used to perform other procedures, surgical or non-surgical, or may be used in industrial applications or other applications.

It is contemplated that the surgical saw assembly 20 may be coupled to a surgical system 24 which comprises a navigation system 25 including a localizer 28 and tracking devices 30, one or more displays 32, and a robotic system 34 comprising a manipulator including a robotic arm 36 and a robot base 38. The robotic arm 36 can include a plurality of links 26 serially extending from the base link to a distal end. The arm links pivot/rotate about a plurality of joints in the robotic arm 36. The surgical saw assembly 20 can be connected to the distal end of the robotic arm 36. The robotic arm 36 may be capable of moving the surgical saw assembly 20 in multiple degrees of freedom, e.g., five or six degrees of freedom. The robotic system 34 can include any number of arms 36. The manipulator may alternatively have a parallel arm configuration, or any other suitable manipulator configuration. Possible arrangements of the robotic system 34 and the tool are described in U.S. Pat. No. 9,119,655, filed on Aug. 2, 2013, entitled, "Surgical Manipulator Capable of Controlling a Surgical Instrument in Multiple Modes," and U.S. Patent Application Publication No. US 2019/0083191, entitled "Robotic Cutting Systems And Methods For Surgical Saw Blade Cutting On Hard Tissue", filed on Sep. 14, 2018, the disclosures of which are hereby incorporated by reference. The robotic system 34 and the tool(s) attached thereto may be arranged in alternative configurations.

In some examples, the robotic system 34 can be or include a hand held manipulator where the base is a base portion of a tool (e.g., a portion held free hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). An example of a hand-held manipulator which can be utilized with the systems, methods, and techniques described herein can be like that described in PCT application No. PCT/US2020/042128, entitled "Robotic Hand-Held Surgical Instrument Systems and Methods", filed on Jul. 15, 2020, the entire contents of which are hereby incorporated by reference.

A robotic controller 40 is coupled to the robotic system 34 to provide control of the robotic arm 36 or guidance to the surgeon during manipulation of the surgical saw assembly 20. In one example, the robotic controller 40 is configured to control the robotic arm 36 (e.g., joint motors thereof) to provide haptic feedback to the user via the robotic arm 36. This haptic feedback helps to constrain or inhibit the surgeon from manually manipulating (e.g., moving) the surgical saw assembly 20 beyond predefined virtual boundaries associated with the surgical procedure. Such a haptic feedback system and associated haptic objects that define the virtual boundaries are described, for example, in U.S. Pat. No. 8,010,180, which is hereby incorporated by reference herein in its entirety. In one example, the robotic system 34 comprises the RIO™ Robotic arm 36 Interactive Orthopedic System manufactured by MAKO Surgical Corp.

In some examples, the robotic arm 36 acts autonomously based on predefined tool paths and/or other predefined movements to perform the surgical procedure. Such movements may be defined during the surgical procedure and/or before the procedure. In further examples, a combination of manual and autonomous control is utilized. For example, a robotic system 34 that employs both a manual mode in which a user manipulates the surgical saw assembly 20 by applying force to the surgical saw assembly 20 to cause movement of the robotic arm 36 and a semi-autonomous mode in which the user holds a pendant to control the robotic arm 36 to autonomously follow a tool path is described in U.S. Pat. No. 9,566,122, hereby incorporated by reference herein in its entirety.

The navigation system 25 is set up to track movement of various objects in the operating room. Such objects include, for example, the surgical saw assembly 20, the patient's anatomy of interest, e.g., the femur F and tibia T, and/or other objects. The navigation system 25 tracks these objects for purposes of displaying their relative positions and orientations to the surgeon and, in some cases, for purposes of controlling or constraining manual manipulation of the surgical saw assembly 20 relative to virtual boundaries associated with the patient's anatomy.

The navigation system 25 can include a cart assembly 42 that houses a navigation controller 44. The navigation controller 44 and the robotic controller 40 collectively form a control system of the robotic system 34. A navigation interface is in operative communication with the navigation controller. The navigation interface can include the displays 32 that are adjustably mounted to the cart assembly 42. Input devices such as a keyboard and mouse can be used to input information into the navigation controller or otherwise select/control certain aspects of the navigation controller. Other input devices are contemplated including head-mounted devices, a touch screen or voice-activation.

The localizer 28 communicates with the navigation controller. In the example shown, the localizer 28 is an optical localizer and includes a camera unit (one example of a sensing device). The camera unit has an outer casing that houses one or more optical position sensors. In some examples at least two optical sensors are employed, sometimes three or more. The optical sensors may be separate charge-coupled devices (CCD). The camera unit is mounted on an adjustable arm to position the optical sensors with a field of view of the below discussed tracking devices 30 that, ideally, is free from obstructions. In some examples the camera unit is adjustable in at least one degree of freedom by rotating about a rotational joint. In other examples, the camera unit is adjustable about two or more degrees of freedom.

The localizer 28 includes a localizer controller in communication with the optical sensors to receive signals from the optical sensors. The localizer 28 controller communicates with the navigation controller 44 through either a wired or wireless connection. One such connection may be a serial bus interface standard for high-speed communications and isochronous real-time data transfer. The connection could also use a company specific protocol. In other examples, the optical sensors communicate directly with the navigation controller 44.

Position and orientation signals and/or data are transmitted to the navigation controller 44 for purposes of tracking the objects. The cart assembly 42, the display 32$s$, and the localizer 28 may be like those described in U.S. Pat. No. 7,725,162 to Malackowski, et al. issued on May 25, 2010, entitled "Surgery System," hereby incorporated by reference.

The navigation controller 44 can be a personal computer or laptop computer, or any other suitable form of controller. Navigation controller 44 has the display 32$s$, central processing unit (CPU) and/or other processors, memory (not shown), and storage (not shown). The navigation processors can be any type of processor, microprocessor or multi-processor system. The navigation controller 44 is loaded with software as described below. The software converts the signals received from the localizer 28 into data representative of the position and orientation of the objects being tracked.

Navigation system 25 includes the plurality of tracking devices 30, also referred to herein as trackers 30. In the illustrated example, trackers 30 are coupled to separate bones of the patient, e.g., the femur F and tibia T. In some cases, the trackers 30 are firmly affixed to sections of bone via bone screws, bone pins, or the like. In other cases, clamps on the bone may be used to attach the trackers 30. In further examples, the trackers 30 could be mounted to other tissue types or parts of the anatomy. The position of the trackers 30 relative to the anatomy to which they are attached can be determined by registration techniques, such as point-based registration in which a digitizing probe P (e.g., navigation pointer) is used to touch off on bony landmarks on the bone or to touch on several points on the bone for surface-based registration. Conventional registration techniques can be employed to correlate the pose of the trackers 30 to the patient's anatomy, e.g., the bones being treated.

In other examples, a separate tracker could be fixed to the surgical saw assembly 20, e.g., integrated into the surgical saw assembly 20 during manufacture or may be separately mounted to the surgical saw assembly 20 in preparation for the surgical procedure. In any case, a working end of the surgical saw assembly 20 is being tracked. The working end may be a distal end of an accessory of the surgical saw assembly 20.

In the illustrated example, the trackers 30 are passive trackers 30. In this example, each tracker has at least three passive tracking elements or markers M for reflecting light from the localizer 28 back to the optical sensors. In other examples, the trackers 30 are active trackers 30 and may have light emitting diodes or LEDs transmitting light, such as infrared light to the optical sensors. Based on the received optical signals, navigation controller 44 generates data indicating the relative positions and orientations of the trackers 30 relative to the localizer 28. In some cases, more or fewer markers may be employed. For instance, in cases in which the object being tracked is rotatable about a line, two markers can be used to determine an orientation of the line by measuring positions of the markers at various locations about the line. It should be appreciated that the localizer 28 and trackers 30, although described above as utilizing optical tracking techniques, could alternatively, or additionally, utilize other tracking modalities to track the objects, such as electromagnetic tracking, radio frequency tracking, ultrasound tracking, inertial tracking, combinations thereof, and the like.

In other examples, the localizer 28 can be one or more of: radio frequency based for tracking radio-frequency trackers, electro-magnetic based for tracking electro-magnetic trackers, machine-vision based for detecting features (e.g., patterns, surfaces, objects) using a machine vision camera, and/or ultrasound based for detecting objects using an ultrasound imaging system.

Figure 4:
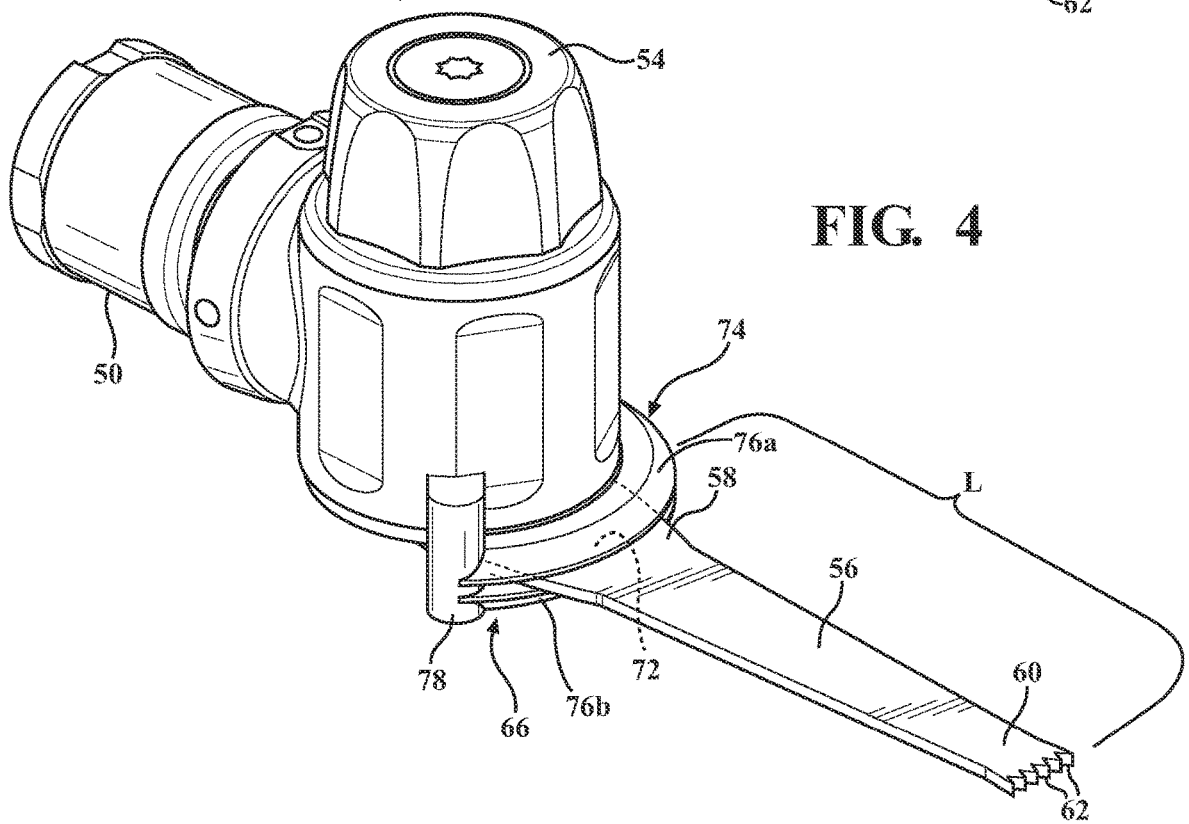
FIG. 4 is a perspective view of the surgical saw assembly of FIG. 3 having the blade guard in a second position, according to one example.
Figures 5, 6:
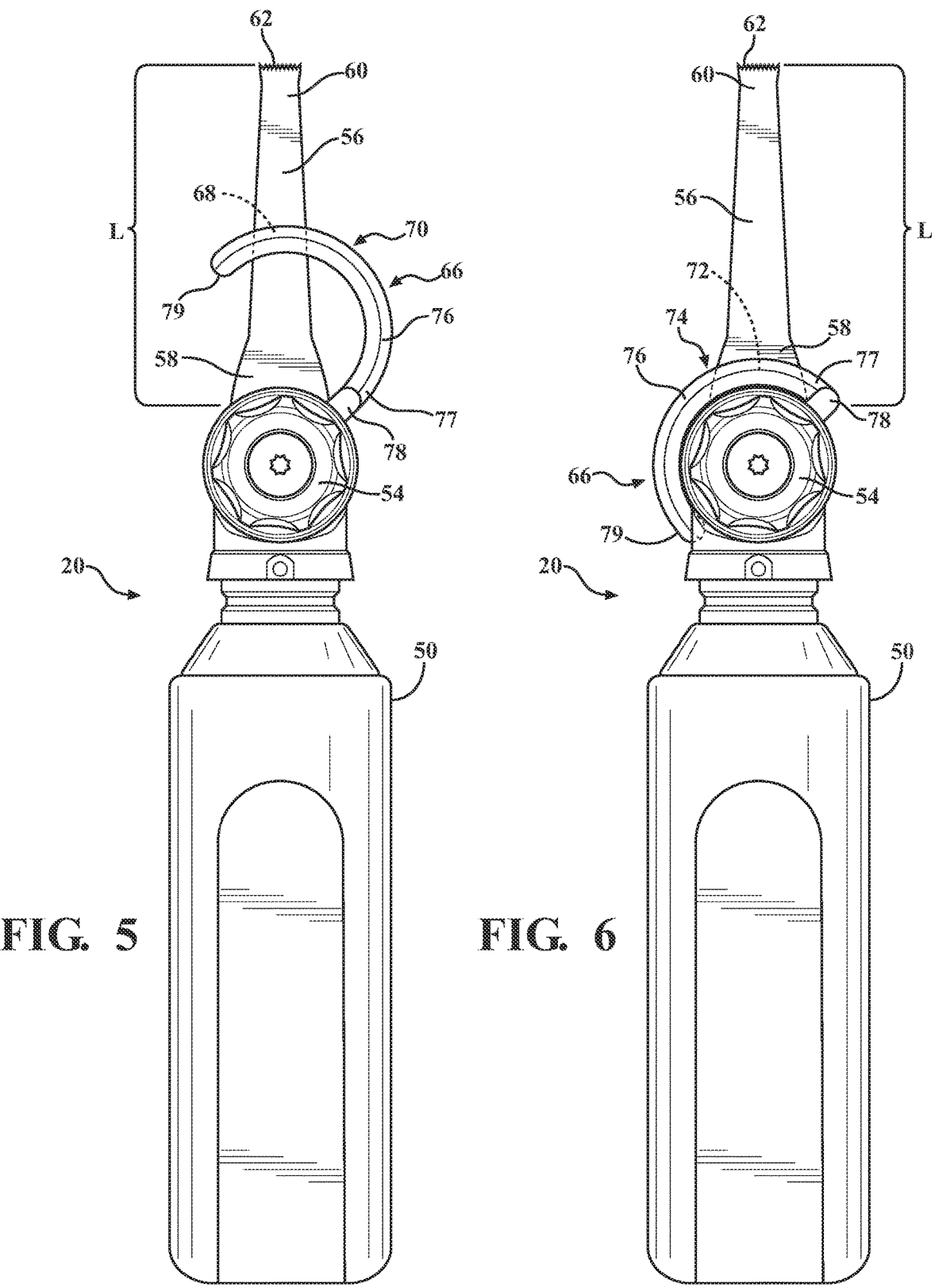
FIG. 5 is a top view of the surgical saw assembly of FIG. 3 having the blade guard in the first position.
FIG. 6 is a top view of the surgical saw assembly of FIG. 3 having the blade guard in the second position.
Figure 7:
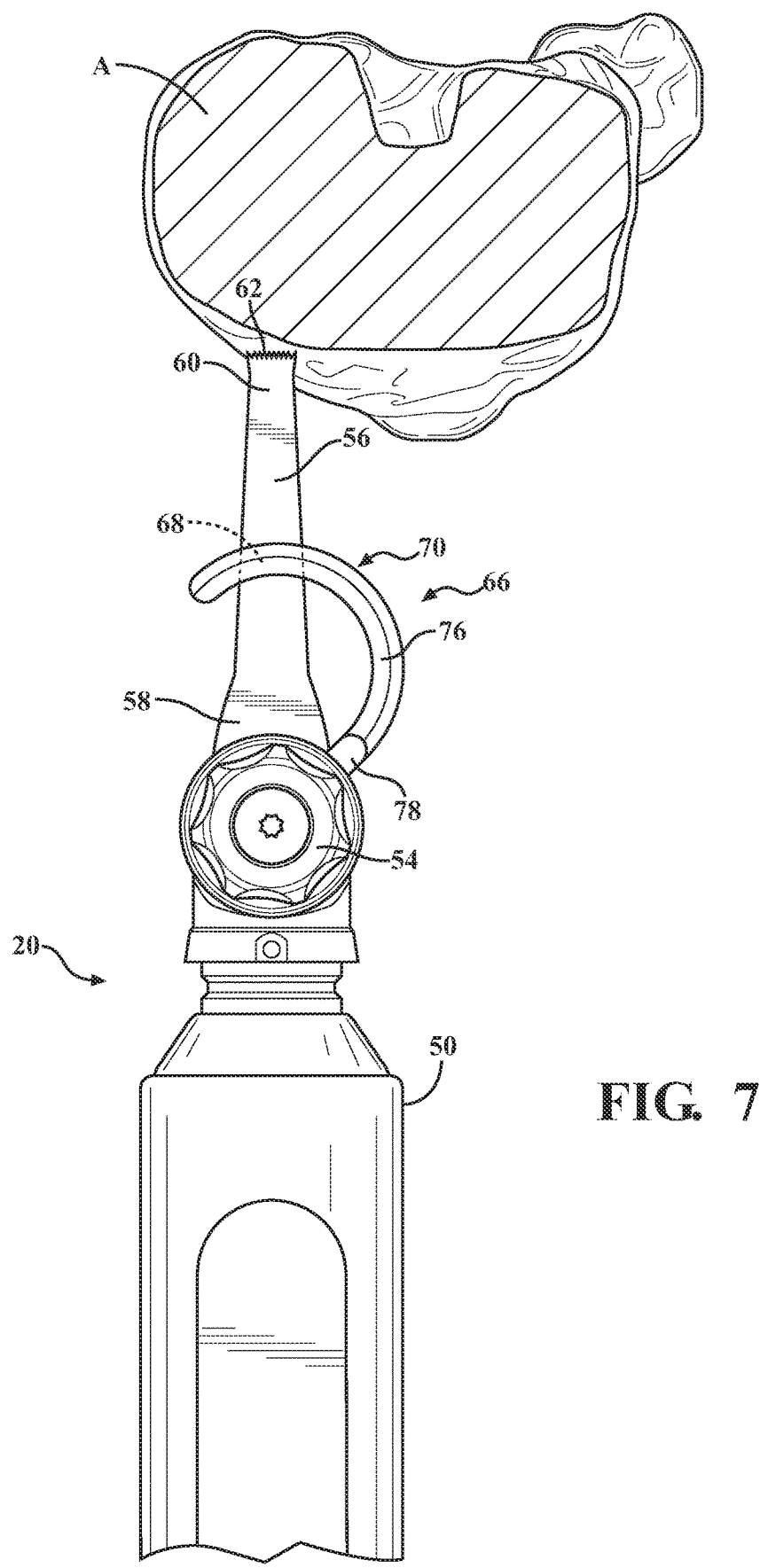
FIG. 7 is a top view of the surgical saw assembly of FIG. 3 in operation, according to one example.

As best illustrated in FIG. 4, the surgical saw assembly 20 includes a base 50 including a motor 52 and a drive hub 54. The motor 52 may be of any suitable type to operate the surgical saw assembly 20, including but not limited to a pneumatic or electrical motor 52. The motor 52 is configured, for instance, to provide oscillating motion to a saw blade 56 of the surgical saw assembly 20 during the surgical procedure. It is contemplated that the motor 52 may provide cyclical linear motion and/or cyclical angular motion, such as used for an oscillating sagittal saw.

The saw blade 56 may be of any size, shape, or type (i.e. straight blade, crescent blade, sagittal cutting, reciprocating, etc.). The saw blade 56 a blade body that includes an attachment portion 58 configured to be removably coupled to the drive hub 54. Opposite the attachment portion 58, the body of the saw blade 56 includes a cutting portion 60 which has a plurality of teeth 62. The body of the saw blade 56 has a length L defined between the attachment portion 58 and the cutting portion 60. In some examples, the saw blade 56 is formed from a single piece of material, such as metal, by stamping and/or machining. The saw blade 56 may be configured to create a kerf with a generally flat face or may be configured to provide a kerf with a rounded profile. However, various configurations have been contemplated. The surgical saw assembly 20 and associated saw blade 56 may be like that described in U.S. Patent Application Publication No. 2017/0348007, filed on Jun. 2, 2017, entitled "Surgical Saw and Saw blade 56 for use therewith," which is hereby incorporated herein by reference. The surgical saw assembly 20 and associated saw blade 56 may also be like that described in U.S. Patent Application Publication No. 2014/0180290, filed on Dec. 21, 2012, entitled "Systems and Methods for Haptic Control of a Surgical Tool," which is hereby incorporated herein by reference.

A desired cutting plane is defined as the plane in which a planar cut is desired to be made with the saw blade 56. In the examples illustrated, the cutting plane is disposed transverse to an outer surface of the hard tissue. More specifically, the outer surface of the hard tissue (e.g., bone) is arcuate or curved such that the cutting plane often extends non-perpendicularly from the outer surface. As a result, merely placing the saw blade 56 on the cutting plane, starting oscillation of the saw blade 56, and then making contact with the outer surface to initiate cutting, without more, will likely result in deflection or skiving of the saw blade 56 along the curved outer surface. The systems and methods described herein can limit such deflection or skiving.

In these systems and methods, virtual objects (such as virtual boundaries), which may also be haptic objects (such as haptic boundaries), may be used to control (e.g., limit and/or constrain) movement of the saw blade 56 by operating the robotic arm 36 in a desired manner to limit deflection or skiving. These virtual/haptic objects may be defined by points, lines, planes, volumes, or the like, and may be 1-D, 2-D, or 3-D. Such virtual/haptic objects may be defined as models and could be solid models (e.g., built with constructive solid geometry or the like), surface models (e.g., surface mesh, etc.), or any suitable form of 3-D model. These objects may be registered pre-operatively or intraoperatively to images/models (e.g., CT scans, X-ray images, MRI images, 3-D models, etc.) of the patient's anatomy that are mapped to the patient's actual anatomy using well-known registration techniques. Thus, in some examples, the locations of the virtual/haptic objects described herein are mapped to the patient's anatomy to control movement of the saw blade 56 in a manner that limits deflection or skiving of the saw blade 56. For example, the robotic system 34 may be controlled based on a haptic boundary that defines a desired plane in which the saw blade 56 should be constrained. In this case, the robotic controller 40 operates the robotic arm 36 so that the saw blade 56 is confined by the haptic boundary to stay on the desired plane. The manner of controlling the robotic system 34, e.g., the robotic arm 36, based on such virtual/haptic objects is described, for example, in U.S. Pat. Nos. 8,010,180, 9,119,655, or U.S. Patent Application Publication No. 2014/0180290, all of which are hereby incorporated herein by reference.

In some procedures, such as during a total knee procedure, several planar cuts are made to the hard tissue, and any of these planar cuts may employ the methods described herein. In some examples, cutting may be completely through the hard tissue or only partially through the hard tissue such that the cut is finished when a pre-determined final depth is reached. The cutting plane may be defined pre-operatively by the surgeon, such as by defining desired planar cuts on a virtual 3-D model of the hard tissue created using pre-operative images taken of the hard tissue. The desired planar cuts may also be defined by the shape of the implant and a 3-D model of the implant. The cutting plane may be defined intraoperatively by the surgeon, or automatically by the control system. A position and orientation of the cutting plane may be tracked by the navigation system 25 as the hard tissue moves during the surgical procedure by virtue of the tracker attached to the hard tissue and registration of the tracker to the hard tissue. The location of the cutting plane may be tracked by virtue of being mapped to the 3-D model that includes the cutting plane. The robotic system 34 can accommodate movement of the cutting plane and autonomously adjust its own positioning as needed to maintain any desired relationship to the hard tissue required in the methods described herein, such as staying on a desired plane with respect to the hard tissue when necessary. Such control may be accomplished using the robotic controls described, for example, in U.S. Pat. Nos. 8,010,180, 9,119,655, or U.S. Patent Application Publication No. 2014/0180290, all of which are hereby incorporated herein by reference.

II. Example Blade Guard Overview

As best shown in FIGS. 3-16, the surgical saw assembly 20 further includes a blade guard 66. The blade guard 66 is configured to provide support to the saw blade 56, e.g., during operation of the robotic system 34. As shown in the Figures, the blade guard 66 is coupled to the surgical saw assembly 20, and more specifically, coupled to the base 50. Alternatively, the blade guard 66 can be coupled directly to the saw blade 56. Among other advantages which will be described below, the blade guard 66 provides stability to the saw blade 56 to withstand transverse forces from the hard tissue acting on the saw blade 56 during operation that may otherwise cause skiving or other undesirable movement of the saw blade 56. Additionally, use of the blade guard 66 allows a thinner saw blade 56 to be used owing to the additional support being given to the saw blade 56 by the blade guard 66.

The blade guard 66 comprises one or more rotatable members 76, which can be rigid or flexible, or a combination of rigid and flexible. The rotatable members 76 can be made of any suitable material, such as metal, steel, hard plastic, rubber, or the like. The description below which references the blade guard 66 can apply fully to the description of the rotatable member(s) 76. The blade guard 66 can be single use and disposable or can be multi-use and sterilizable.

As best shown in FIGS. 3-12, the blade guard 66 may have a pivot 78. The pivot 78 may be located adjacent the attachment portion 58 or located to the side of the saw blade 56. In the examples shown, the proximal end 77 of the rotatable member 76 is located at and connected to the pivot 78. In another example, shown in FIGS. 13-16, the blade guard 66 may include the pivot 78 adjacent the top surface of the attachment portion 58 of the saw blade 56. The pivot 78, if applicable, can be located at any suitable location, including on the saw blade 56 itself. The pivot 78 can include any suitable components (such as gears, cams, springs, nuts, bolts, etc.) to enable the blade guard 66 to rotatably pivot.

The blade guard 66 or rotatable member(s) 76 may be of any shape or size. The blade guard 66 or rotatable member(s) 76 can be arcuate, bent, and/or curved. In one implementation, the blade guard 66 has a circular shape with an arc length between 90 degrees and 270 degrees. For example, in FIGS. 3 and 4, the blade guard 66 has an arc length of approximately 180 degrees. The blade guard 66 can be U-shaped or C-shaped (e.g., FIGS. 11 and 12), hook-shaped (e.g., FIGS. 13 and 14), pear-shaped (e.g., FIGS. 15 and 16), and/or snail or cam-shaped, or any derivate or equivalents thereof. In some examples, the rotatable member 76 may have more than one proximal end 77 and/or more than one distal end 79. For example, the rotatable member 76 may have arcuate, bent, and/or curved versions of an F-shape, T-shape, W or M-shape, X-shape, or any other irregular shape. The size and/or shape of the blade guard 66 or rotatable member(s) 76 can depend on many factors, such as, but not limited to, the length L of the saw blade 56, the anticipated depth of cut, the nature of the procedure, or surgeon preferences.

The blade guard 66 or rotatable member(s) 76, regardless of its shape, exhibits a front edge profile, which is the portion of the blade guard 66 that is configured to interact with the surface of the anatomy A. The front edge profile can be defined anywhere along the blade guard 66 at, or between, the distal end 79 and the proximal end 77. The front edge profile is generally curved, contoured, angled, convex, or bent. In other words, the front edge profile is not completely flat, straight, or linear along the entire length of the front edge profile. This way, for passive configurations, when the front edge profile of the blade guard 66 interacts with the complex surface of the anatomy A, the blade guard 66 is configured to smoothly rotate due to forces applied therebetween. Alternatively, or additionally, for configurations when the blade guard 66 is actively controlled, the front edge profile will exhibit a smooth interaction with the surface of the anatomy A during rotation of the blade guard 66. In either instance, the rotatable movement of the blade guard 66 and the curved front edge profile will enable the blade guard 66 to follow a path of movement or trajectory that is more precisely tailored to the specific geometry of the anatomy A. This path of movement can be arcuate, contoured, curved, bent, or any irregular or non-linear path depending on the surface of the anatomy A and the geometry of the front edge profile.

Figure 3:
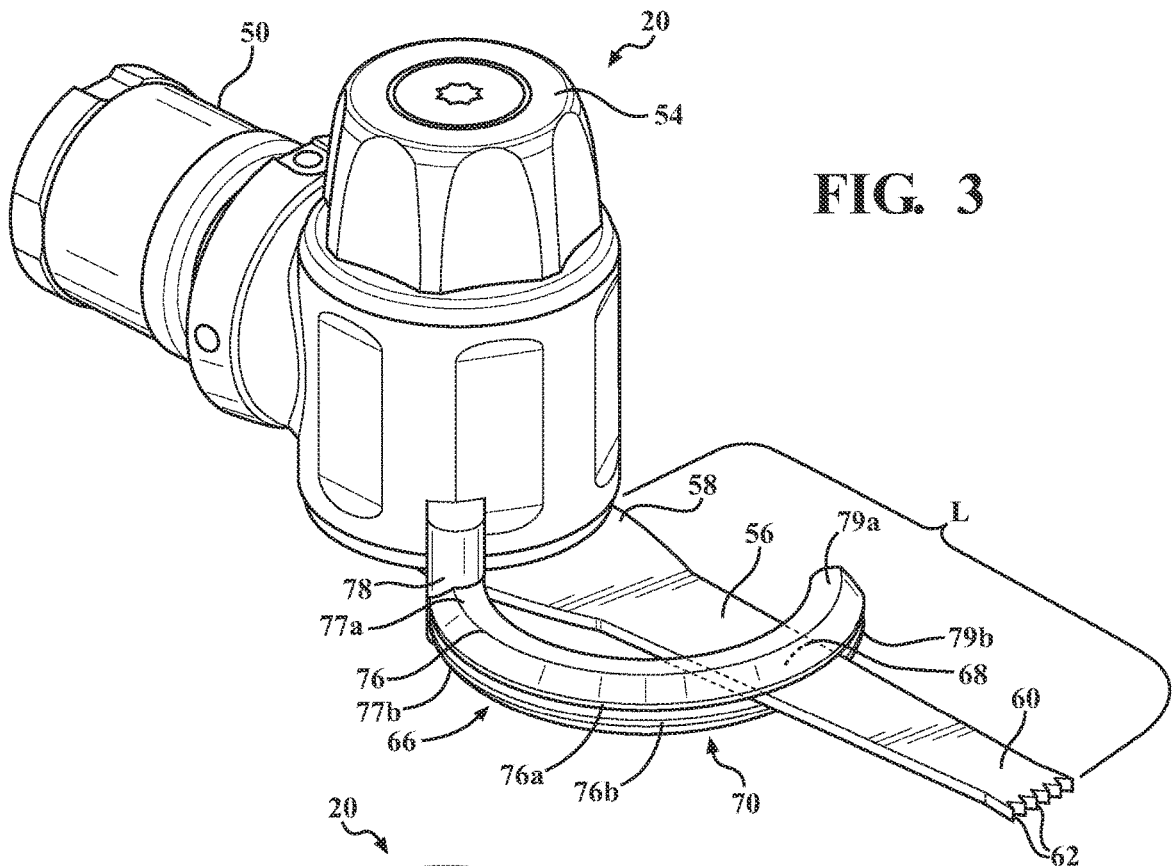
FIG. 3 is a perspective view of one example of the surgical saw assembly having a blade guard in a first position, according to one example.

In the example illustrated in FIGS. 3-16, the blade guard 66 is rotatably movable between a first position 70 and a second position 74. As shown, for example, in FIG. 3, the first position 70 the blade guard 66 is configured to support the saw blade 56 at a first location 68 along the length L of the saw blade 56. As shown in FIG. 4, for example, in the second position 74 the blade guard 66 is configured to support the saw blade 56 at a second location 72 along the length L of the saw blade 56. The first location 68 is further from the attachment portion 58 of the saw blade 56 than the second location 72. The blade guard 66 moves between these positions along the arcuate or curved path of movement. The blade guard 66 can support the saw blade 56 at any location along the length L other than the first and second locations 68, 72 and according to any other position other than the first and second positions 70, 74. In other words, the blade guard 66 is not intended to be limited for use only at the first and second positions 70, 74 and can indeed operate at any position therebetween or exceeding these positions 70, 74. The first position 70 can be a fully extended position (as shown in FIG. 3) or a partially extended position of the blade guard 66. The second position 74 can be a fully retracted position (as shown in FIG. 4) or a partially retracted position of the blade guard 66.

The term "location" as it relates to the saw blade 56 can include a point, area, surface area, volume, and/or general region. In other words, the term "location" is not limited to a discrete point but can be defined as the general region at which the blade guard 66 supports by the saw blade 56. The location at which the blade guard 66 supports the saw blade 56 can continuously change (position, size, shape, area) throughout movement of the blade guard 66.

In some implementations, such as shown in FIGS. 4-9, 11 and 12, when the blade guard 66 is in the first position 70, the blade guard 66 may not support any other part of the saw blade 56 other than the support provided at the first location 68. Alternatively, in some implementations, such as shown in FIGS. 4-9, when the blade guard 66 is in the first position 70, the blade guard 66 may support any other part of the saw blade 56 other than the support provided at the first location 68. In other words, it is possible for the blade guard 66 to provide support the saw blade 56 at more than one location simultaneously in the first position 70. For instance, in FIG. 13, the blade guard 66 being in the first position 70 supports the saw blade 56 at the first location 68 while also supporting the saw blade 56 along at a supplemental region 73. The supplemental region 73, in this example, is an area of the saw blade 56 that extends from the first location 68 to the attachment portion 58 of the saw blade 56. Similarly, in FIG. 15, the blade guard 66 is shown providing support at the first location 68 as well as the supplemental region 73. The area and/or location of the supplemental region 73 being supported can be consistent or can change depending upon the geometry and position of the blade guard 66. The blade guard 66 can provide support to the supplemental region 73 in any position in addition to the first position 70.

In some implementations, the blade guard 66 may be fully retracted in the second position 74 such that the second location 72 does not lie along the length L of the saw blade 56. In such scenarios, it is contemplated that the blade guard 66 need not provide support to the saw blade 56 based on the understanding that the saw blade 56 may be substantially supported by the anatomy A which is being cut.

In one example, the blade guard 66 is flexible and configured to flex between the first position 70 and the second position 74. The flexibility may be inherent to the blade guard 66 rotatable member 76. For example, the rotatable member 76 may be configured as an arcuate, bent, and/or curved shaped leaf spring have an appropriate spring constant. In such instances, the rotatable member 76 may be fixed to at its proximal end with or without a pivot 78. Alternatively, the rotatable member 76 can be rigid and the flexibility is enabled by a spring that is coupled to the rotatable member 76. The spring can be coupled at or between any location(s) of the rotatable member 76. In one example, the spring is a torsional spring that is disposed within the pivot 78 and the rotatable member 76 is coupled at its proximal end 77 to the torsional spring. In another example, the spring can be coupled between the proximal end 77 and another location on the rotatable member 76. The spring can have any configuration, such as compression, extension, leaf, torsion, or the like.

Movement of the blade guard 66 may be controlled by the control system of the robotic system 34. For example, an actuator A (e.g., electric motor 52) may be coupled to the blade guard 66 to rotate or flex the blade guard 66 between the first position 70 and the second position 74. It is also contemplated that movement of the blade guard 66 may be based on a tracked position of the surgical saw assembly 20 and/or anatomy A from the navigation sensor, or based on a distance sensor (e.g. laser, camera, radar, lidar, etc.) disposed on the surgical saw assembly 20 which measures distance to the anatomy A. In some instances, when using an actuator to move the blade guard 66, the navigation system 25 monitors movement of the saw blade 56 or saw assembly 20 relative to a registered model of the anatomy A. The control system operates the actuator to move the blade guard 66 proactively or reactively in a coordinated manner so that the saw blade 56 is supported as desired, for example, according to surgical planning or other operational parameters.

It is also contemplated that the blade guard 66 may be manually operated such as through manual trigger or other actuation method. In one example the blade guard 66 includes a biasing member which is configured to bias the blade guard 66 towards the first position 70. The biasing device is arranged so that when the blade guard 66 engages the hard tissue and the saw blade 56 is further driven into the hard tissue, the blade guard 66 pivots or flexes towards the second position 74, albeit while continuously being biased toward the hard tissue by the biasing device. In other words, the blade guard 66 may be configured to move from the first position 70 to the second position 74 in response to force applied between the blade guard 66 and the anatomy A to be cut. The first position 70 can be defined according to various ways. In one implementation, the first position 70 can be set by a one-way interference, where the biasing member pushes the blade guard 66 away until the blade guard 66 interferes with a bumper or stop that is provided with the blade guard 66. In another implementation, the first position 70 can be set using a detent or pawl that holds the blade guard 66 in the first position 70, wherein the detent retention force can be overcome by force applied by the surface of the anatomy. In another example, the first position 70 can be the inherent physical or mechanical limit of the biasing member, or the inherent at-rest state of the biasing member. Similarly, the second position 74 can be defined by a one-way interference, by a bumper, stop, detent, pawl or by the inherent physical limit of the biasing member. Such configurations can also be utilized to defined various positions of the blade guard 66 other than the first and second positions 70, 74.

In some implementations, the blade guard 66 can include a manual interface that is adapted to enable the operator to manually adjust or control the blade guard 66. This interface can be a rotatable knob or dial that incrementally changes the position of the blade guard 66 as desired. The adjustment could be an incremental retraction or extension of the blade guard 66, locking the blade guard 66 in a static position (e.g., fully extended fully retracted, or any location therebetween), or setting the limits on movement of the blade guard 66. In other instances, the manual interface could be used to move the blade guard 66 to a position, wherein the position is not locked, but can be overcome by force applied by the surface of the anatomy. In some examples, the blade guard 66 is easily detachable and attachable to the assembly should use of the blade guard 66 not be desired for certain steps of the procedure.

The blade guard 66 is configured to support one or both of the top surface and the bottom surface of the saw blade 56 between and at the first position 70 and the second position 74. For example, in the implementations shown in FIGS. 11-16, the blade guard 66 can comprise only one rotatable member 76. In these examples, the rotatable member 76 is disposed above the saw blade 56. Alternatively, the rotatable member 76 can be arranged to be below the saw blade 56. In some examples, a surgeon or staff can manually and releasably attach the rotatable member 76 to the surgical saw assembly 20. The surgical saw assembly 20 can provide mechanical connections to the rotatable member 76 to enable the possibility for installing the rotatable member(s) 76 above and/or below the saw blade 56 based on surgical preference or surgical procedure. In such instances, the surgical saw assembly 20 can be provided as a kit which includes the blade guard 66 and rotatable member(s) 76 attachments. It is also contemplated that the blade guard 66 may engage the saw blade 56 in any manner configured to provide support and rigidity to the saw blade 56.

In another example, as best shown in FIGS. 3 and 4, the blade guard 66 supports both the top and bottom surfaces of the saw blade 56. Here, the blade guard 66 may comprise at least two rotatable members 76a, 76b, which are disposed above and below the saw blade 56. Here, the blade guard 66 may provide a passage or slot between the rotatable members 76a, 76b sized to receive the saw blade 56. The saw blade 56 is received in a sliding manner such that the saw blade 56 is disposed between and constrained from flexing at the location overlapped by the rotatable members 76a, 76b, while enabling the saw blade 56 to slide/oscillate within the passage or slot. In this example, the rotatable members 76a, 76b are each connected at a proximal end 77a, 77b, respectively, to the surgical saw assembly 20. The rotatable members 76a, 76b are disconnected from one another at their distal ends 79a, 79b, respectively, thereby leaving a gap between their distal ends 79a, 79b. This way, the blade guard 66 with rotatable members 76a, 76b can slide over the saw blade 56 using a wide angle range without abutting a side of the saw blade 56, for example, if the blade guard 66 were to move (clockwise) beyond the first position 70 shown in FIG. 3. Alternatively, the rotatable members 76a, 76b can be connected to one another at their distal ends 79a, 79b, respectively, such that a piece connects between their distal ends 79a, 79b.

The rotatable members 76a, 76b can both be above the saw blade 56, both below the saw blade 56 or above and below the saw blade 56. The rotatable members 76a, 76b can be the same shape or different shapes. For example, when different, one rotatable member 76 can be half-circle shaped while the other rotatable member 76 is pear-shaped. The rotatable members 76a, 76b can be the same or different configurations. For example, when different, one rotatable member 76 can be rigid and the other rotatable member 76 can be flexible. The rotatable members 76a, 76b can be operated in the same or different manner. For example, when different, one rotatable member 76 can be spring biased and the other rotatable member 76 can be actively controlled. The rotatable members 76a, 76b can be moveable in the same or different manner. For example, one rotatable member 76 can rotate clockwise and the other rotatable member 76 can rotate counterclockwise.

The rotatable members 76a, 76b can be moved simultaneously or dependent on each other. In other words, both rotatable members 76a, 76b may be permanently configured or otherwise controlled to move together. This may be implemented by a rigid connection between the rotatable members 76a, 76b or by active and synchronous control of the rotatable members 76a, 76b. The rotatable members 76a, 76b can be moved together to support a common location (above and below) the saw blade 56. This may implemented by configuring the rotatable members 76a, 76b with identical shapes (as shown in FIG. 3 for example) and/or by ensuring that the rotatable members 76a, 76b, regardless of whether they have identical or different shapes, move to the common location. For example, the rotatable members 76a, 76b can actively and synchronously controlled to arrive at the common location, regardless whether the rotatable members 76a, 76b have the same or different shapes.

Alternatively, the rotatable members 76a, 76b can be moved non-simultaneously or independently of one another. In other words, one rotatable member 76 may be moved while the other rotatable member 76 remains stationary or moves in a different manner. This may be implemented by separate and independent connections for each of the rotatable members 76a, 76b, separation between the rotatable members 76a, 76b, and/or by active and non-synchronous control of the rotatable members 76a, 76b. Alternatively, or additionally, the rotatable members 76a, 76b can support different locations of the saw blade 56. This may be implemented by separate and independent connections for each of the rotatable members 76a, 76b, by active and non-synchronous control of the rotatable members 76a, 76b, and/or by providing different shapes for the rotatable members 76, 76b.

The above-described features of the rotatable members 76a, 76b can be dependent on or configured based on several factors, such as the nature of the procedure (e.g., type of cut or bone), surgeon preferences, operational parameters of the saw assembly 20, or the like. Where applicable, any of the above-described features of the rotatable members 76a, 76 can be applied fully to instances where the blade guard 66 has only one rotatable member 76.

In some implementations, the rotatable member(s) 76 are shaped to wrap around a corresponding part (e.g., drive hub 54, or base 50) of the saw assembly 20 in the second position 74, which in this instance is a fully retracted position. In this manner, a substantial portion of the blade guard 66 can be tucked away thereby reducing the footprint of the blade guard 66 and avoiding interference with the surgical site. This configuration may necessitate that the corresponding part of the saw assembly 20, which interacts with the blade guard 66, is correspondingly shaped. For example, in FIG. 10, the rotatable member 76 of the blade guard 66 is semi-circular in shape and the drive hub 54 is circular shaped. When the blade guard 66 is moved to the second position 74, distal end(s) 79a, 79b of the rotatable member(s) 76 are disposed adjacent the drive hub 54 opposite from the pivot 78 and out of the way. The blade guard 66 in FIGS. 11-12 operates similarly such that the U-shaped rotatable member 76 is shaped to wrap around a rectangular profiled drive hub 54 in in the second position 74, however, the rectangular portion is shaped to receive a rectangular shaped base 50. Any other shapes of the rotatable member(s) 76 and corresponding port of the saw assembly 20 are contemplated to enable implementation of this wrap around feature.

Figure 8:
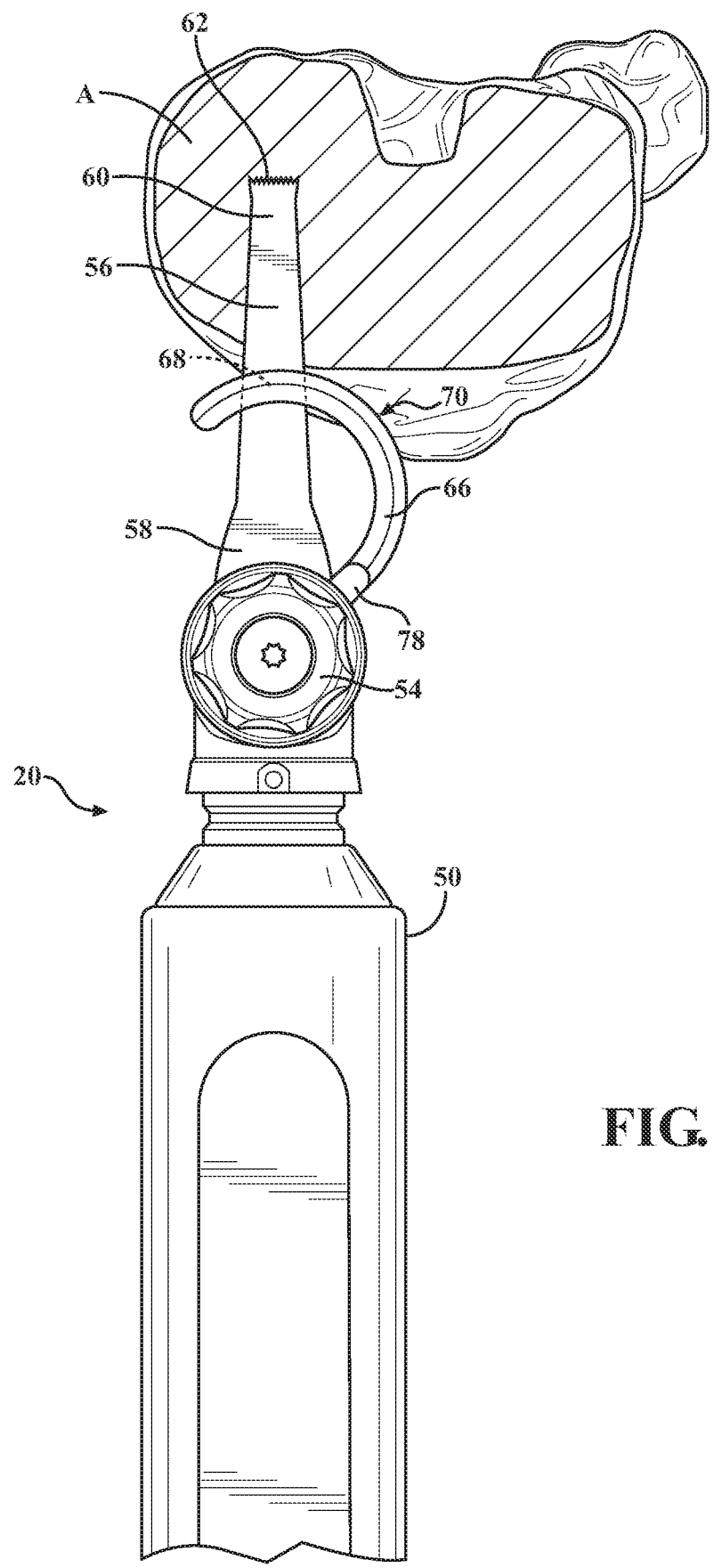
FIG. 8 is a top view of the surgical saw assembly of FIG. 3 in operation.
Figure 9:
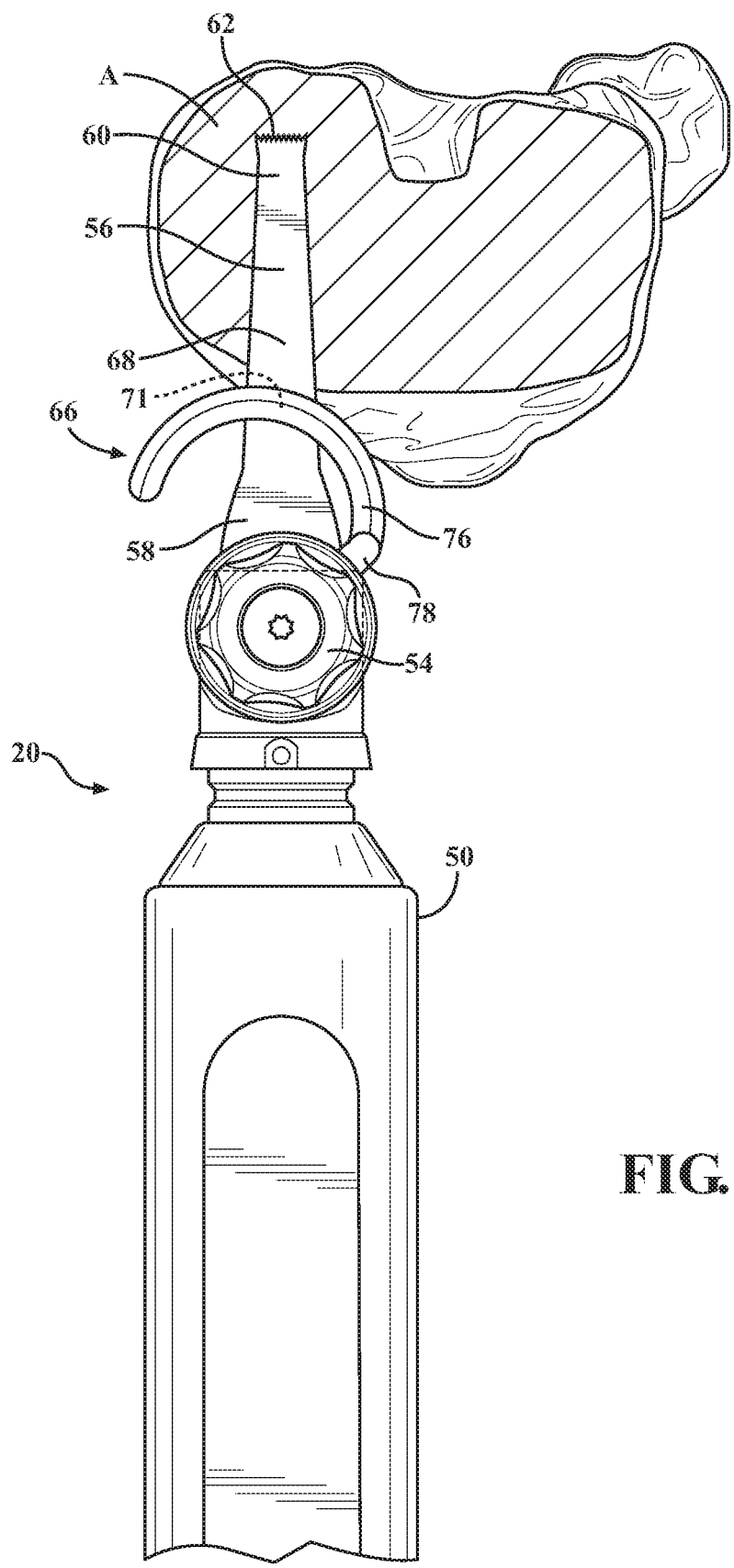
FIG. 9 is a top view of the surgical saw assembly of FIG. 3 in operation.
Figure 10:
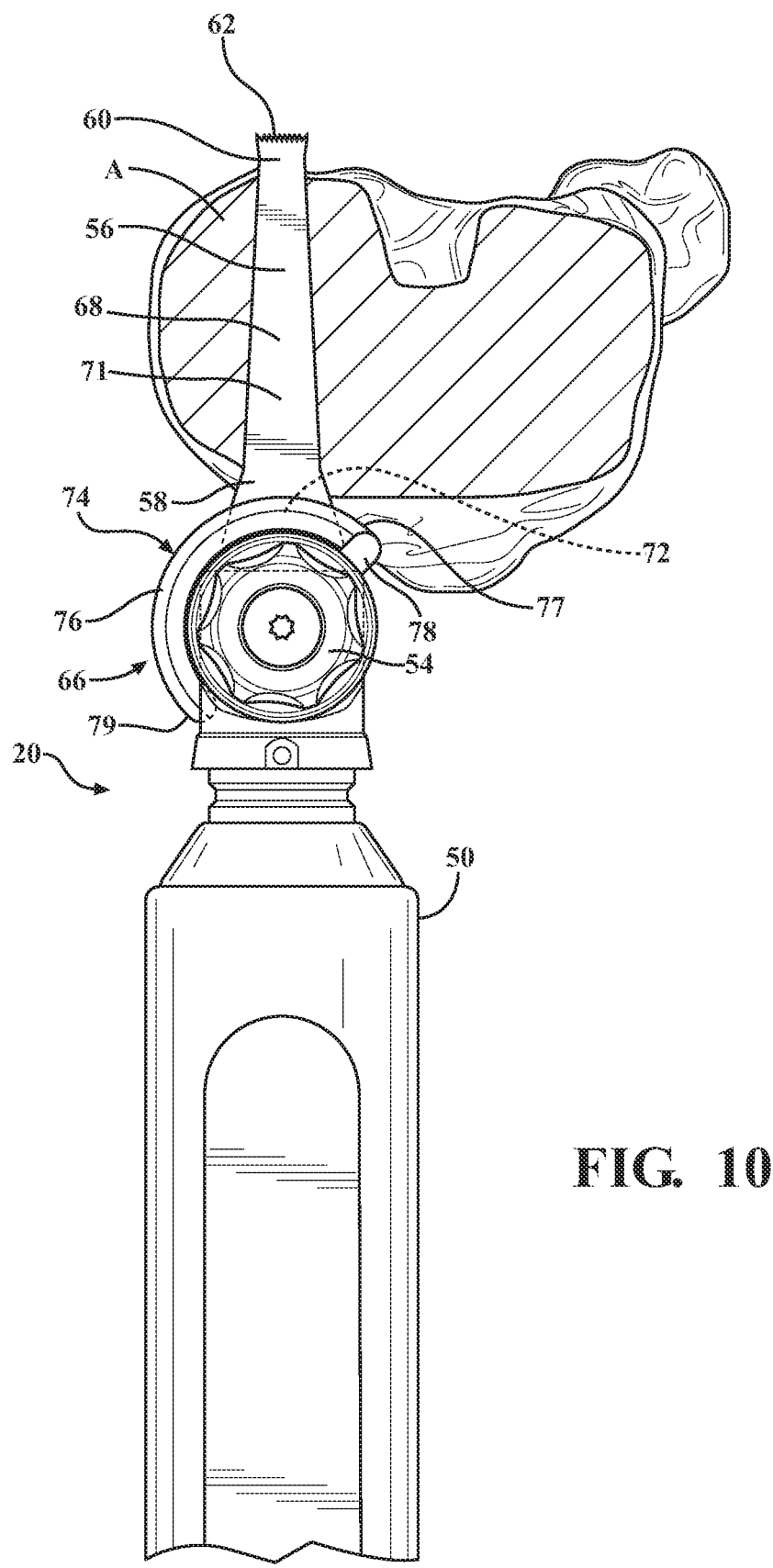
FIG. 10 is a top view of the surgical saw assembly of FIG. 3 in operation.
Figure 15:
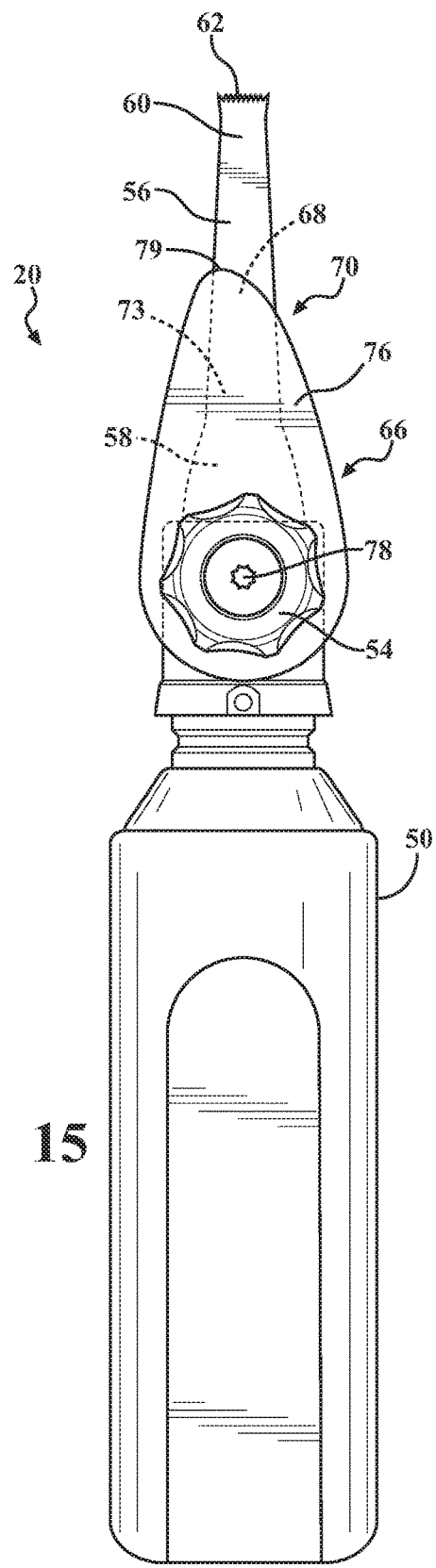
FIG. 15 is a top view of yet another example of a surgical saw assembly having a blade guard in a first position.
Figure 16:
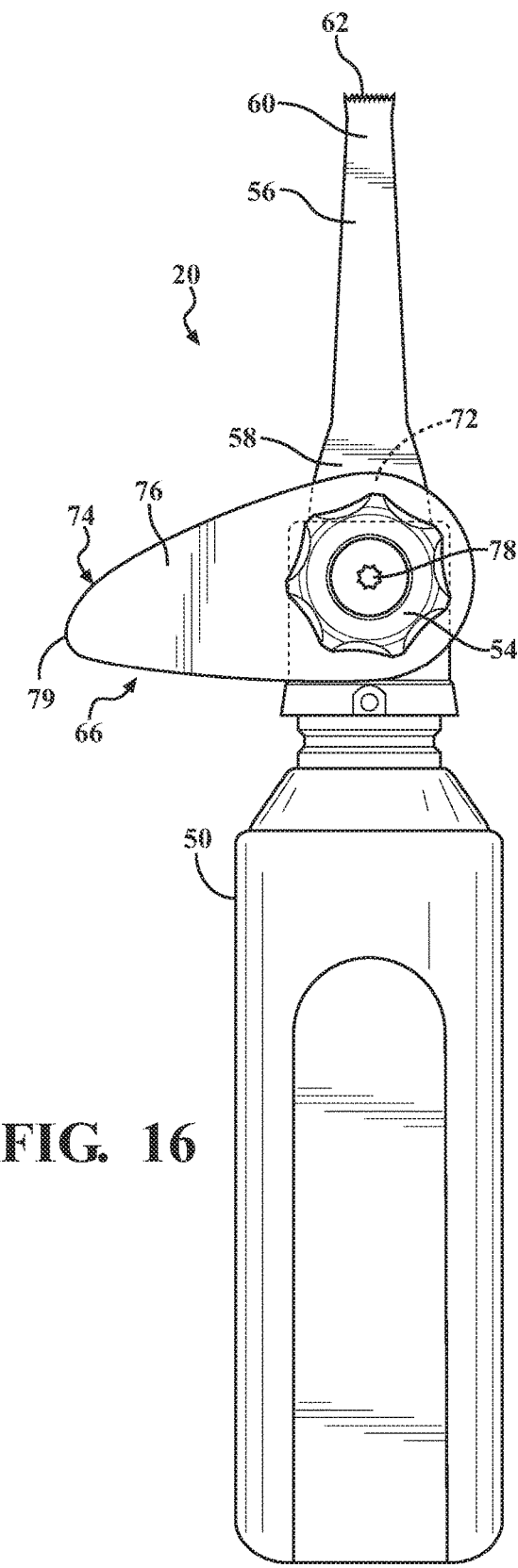
FIG. 16 is a top view of the surgical saw assembly of FIG. 15 having the blade guard in the second position.

A non-limiting example operation of the blade guard 66 is sequentially shown in FIGS. 7-10. Starting at FIG. 7, the surgical saw assembly 20 is aligned with the cutting plane with the blade guard 66 supporting the saw blade 56 in the first position 70, which in this case is a fully extended position. Here, the blade guard 66 stabilizes the saw blade 56 at the first location 68 during the initial entry cut, which is typically most susceptible to skiving or deflection. In FIG. 8, the saw blade 56 is then moved along the cutting plane (either manually or autonomously as previously described). Here, the blade guard 66 continues to support the saw blade 56 at the first location 68 while the portion of the saw blade 56 beyond the first location 68 is supported by surrounding anatomy A which captures the saw blade 56 during the cut. In FIG. 9, the saw blade 56 enters further into the anatomy A, and the blade guard 66 is rotated from the first position 70 to an intermediate position at which the blade guard 66 supports the saw blade 56 at an intermediate location 71. The intermediate location 71 in this example is closer to the attachment portion 58 of the saw blade 56 and in between the first location 68 and the second location 72. In FIG. 10, the saw blade 56 is plunged deeper into the anatomy A and the blade guard 66 is rotated from the intermediate position to the second position 74 whereby the blade guard 66 supports the saw blade 56 at the second location 72 and is substantially moved away from the anatomy A. As described, it may not be desired or required to provide support to the saw blade 56 at the second location 72 considering that the saw blade 56 may be substantially supported by the anatomy A being cut The above example is non-limiting. The example can be applied for passive or active configurations of the blade guard 66. Furthermore, the locations at which the blade guard 66 supports the saw blade 56 can be different from that shown in these examples. For instance, in FIG. 7, it may be desired that the blade guard 66 supports the saw blade 56 at a location that is closer to the cutting portion 60 than what is shown.

In additional implementations, the blade guard 66 and/or surgical blade 56 may include depth markings. The depth markings can indicate to the user how deeply the saw blade 56 has entered the anatomy. The depth markings can alternatively indicate how much the blade guard 66 has been retracted from its fully extended position. In one example, the depth markings could be placed along the front edge profile of the blade guard 66. The depth markings can be defined in view of the known relationship between the cutting portion 60 and the blade guard 66. As the front edge profile interacts with the surface of the anatomy and consequently moves along the non-linear path of movement, the marking on the front edge profile that is coincident with the touch point of the anatomy could be read to indicate the relative depth.

The blade guard 66 provides several benefits over conventional linear guards. The blade guard 66 is more effective and robust than linear guards when making surgical cuts that are not directly normal to the bone surface. The rotatable movement of the blade guard 66 can provide blade support for both linear and rotational (e.g., yaw) movement of the saw blade assembly relative to the anatomy A. Therefore, the blade guard 66 effectively supports the saw blade 56 even when the making cuts that involve rotation. Furthermore, the blade guard 66 can interface with the bone using a curved front edge profile or a front edge that moves along a path of movement that is not linear, which is more suitable for complex bone surfaces. In other words, the interaction between the curved front edge profile and a complex bone surface is smoother than conventional linear blade guards, thereby avoiding flexing or bending of the blade guard 66 which can cause interference with the saw blade. Furthermore, by rotating, the blade guard 66 can utilize lesser components and exhibit a lesser footprint than conventional linear guards. When moving between the first and second positions 70, 74 the blade guard 66 is configured to rotate out of the way of the surgical site more effectively than linear guides, e.g., which require permanent members that can extend into the surgical site. In some implementations, the blade guard 66, in the fully retracted position, is configured to wrap around, or "hug" a component of the surgical saw assembly 20, thereby concealing the blade guard 66 during cutting. In the fully retracted position, the blade guard 66 can be tucked away thereby increasing the maneuverability of the surgical saw assembly 20 relative to the anatomy A.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical saw assembly adapted for cutting an anatomy, comprising:
 a base including a motor and a drive hub;
 a saw blade including a proximal end with an attachment portion configured to be removably coupled to the drive hub, an opposing distal end with a cutting portion comprising a plurality of teeth, and a body being elongated and extending between the proximal end and the opposing distal end; and
 a blade guard being coupled to one or more of the base or the saw blade and being rotatably moveable relative to the saw blade to support the saw blade at one or more locations along the body of the saw blade such that the blade guard is configured to prevent deflection or skiving of the saw blade, and wherein the blade guard comprises a front edge profile that is configured to interact with a surface of the anatomy, and wherein the front edge profile is configured to follow a non-linear path of movement.

2. The surgical saw assembly of claim 1, wherein the front edge profile has a geometry that is at least partially non-linear or at least partially curved.

3. The surgical saw assembly of claim 1, wherein the blade guard is U-shaped, C-shaped, hook-shaped, snail-shaped, or pear-shaped.

4. The surgical saw assembly of claim 1, wherein the blade guard has a rigid body and is configured to rotate about a pivot point that is fixed relative to either the base or the saw blade.

5. The surgical saw assembly of claim 1, wherein the blade guard is flexible and configured to rotatably flex.

6. The surgical saw assembly of claim 1, wherein:
 the blade guard is rotatably moveable between a first position and a second position, wherein in the first position the blade guard is configured to support the saw blade at a first location along the body of the saw blade and in the second position the blade guard is configured to support the saw blade at a second location along the body of the saw blade, the first location being further from the attachment portion than the second location.

7. The surgical saw assembly of claim 6, wherein the blade guard includes a biasing member configured to bias the blade guard to the first position.

8. The surgical saw assembly of claim 7, wherein the blade guard is configured to rotatably move from the first position to the second position in response to force applied between the blade guard and the surface of the anatomy.

9. The surgical saw assembly of claim 6, wherein:
 the blade guard is fully extended in the first position; and
 the blade guard is retracted in the second position.

10. The surgical saw assembly of claim 6, further comprising a controller, and an actuator coupled to the blade guard, and wherein the controller is configured to control the actuator to rotatably move the blade guard between the first position and the second position.

11. The surgical saw assembly of claim 1, wherein the blade guard is configured to wrap around the drive hub.

12. A surgical device for use with a saw blade and being adapted for cutting an anatomy, the surgical device comprising:
 a base including a motor and a drive hub for removably receiving the saw blade; and
 a blade guard being adapted to support the saw blade at one or more locations along an elongated body of the saw blade such that the blade guard is configured to prevent deflection or skiving of the saw blade, the blade guard being coupled to the base and being rotatably moveable, and wherein the blade guard comprises a front edge profile that is configured to interact with a surface of the anatomy and wherein the front edge profile is configured to follow a non-linear path of movement.

13. The surgical device of claim 12, wherein the front edge profile has a geometry that is at least partially non-linear or at least partially curved.

14. The surgical device of claim 12, wherein the blade guard is U-shaped, C-shaped, hook-shaped, snail-shaped, or pear-shaped.

15. The surgical device of claim 12, wherein the blade guard has a rigid body and is configured to rotate about a pivot point that is fixed relative to the base.

16. The surgical device of claim 12, wherein the blade guard is flexible and configured to rotatably flex.

17. The surgical device of claim 12, wherein:
the blade guard includes a biasing member configured to bias the blade guard to a first position; and
the blade guard is configured to rotatably move from the first position to a second position in response to force applied between the blade guard and the surface of the anatomy, the second position being closer to the base than the first position.

18. The surgical device of claim 12, further comprising a controller, and an actuator coupled to the blade guard, and wherein the controller is configured to control the actuator to rotatably move the blade guard.

19. The surgical device of claim 12, wherein the blade guard is configured to wrap around the drive hub.

20. A surgical saw assembly adapted for cutting an anatomy, comprising:

a base including a motor and a drive hub;

a saw blade including a proximal end with an attachment portion configured to be removably coupled to the drive hub, an opposing distal end with a cutting portion comprising a plurality of teeth, and a body being elongated and extending between the proximal end and the opposing distal end; and a blade guard being coupled to one or more of the base or the saw blade and being rotatably moveable relative to the saw blade to support the saw blade at one or more locations along the body of the saw blade such that the blade guard is configured to prevent deflection or skiving of the saw blade, and wherein the blade guard comprises a front edge profile that is configured to interact with a surface of the anatomy and wherein the front edge profile has a geometry that is at least partially curved.

* * * * *